(12) United States Patent
Schwab et al.

(10) Patent No.: US 6,677,495 B1
(45) Date of Patent: Jan. 13, 2004

(54) OLIGOMER MIXTURES DERIVED FROM CYCLOPENTENE; METHOD FOR THE PRODUCTION AND USE THEREOF

(75) Inventors: Peter Schwab, Bad Dürkheim (DE); Martin Schäfer, Ludwigshafen (DE); Arthur Höhn, Kirchheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/331,417

(22) PCT Filed: Dec. 19, 1997

(86) PCT No.: PCT/EP97/07199
§ 371 (c)(1),
(2), (4) Date: Jun. 21, 1999

(87) PCT Pub. No.: WO98/28245
PCT Pub. Date: Jul. 2, 1998

(30) Foreign Application Priority Data

Dec. 23, 1996 (DE) .......................... 196 54 166

(51) Int. Cl.⁷ .............................. C07C 6/06; C07C 6/04
(52) U.S. Cl. .................. 585/645; 585/646; 585/647
(58) Field of Search ................. 585/645, 646, 585/647

(56) References Cited

U.S. PATENT DOCUMENTS

| | | | |
|---|---|---|---|
| 3,527,828 A | 9/1970 | Mango .................... 585/16 |
| 3,622,644 A | 11/1971 | Kubicek et al. ............ 585/375 |
| 3,637,893 A | 1/1972 | Singleton .................. 585/353 |
| 3,652,703 A | 3/1972 | Regier ..................... 585/643 |
| 3,659,008 A | 4/1972 | Kubicek et al. ............ 585/314 |
| 3,660,507 A | 5/1972 | Reusser .................... 585/374 |
| 3,686,136 A | 8/1972 | Doyle ...................... 502/104 |
| 3,691,095 A | 9/1972 | Kroll et al. ............... 502/102 |
| 3,715,410 A | 2/1973 | Ray et al. ................. 585/506 |
| 3,754,046 A | 8/1973 | Calderon et al. ........... 570/191 |
| 3,792,102 A | 2/1974 | Vives ....................... 585/506 |
| 3,798,175 A | 3/1974 | Streck et al. .............. 502/117 |
| 3,836,480 A | 9/1974 | Reusser .................... 502/219 |
| 3,849,509 A | 11/1974 | Streck et al. .............. 526/142 |
| 3,849,513 A | 11/1974 | Doyle ...................... 585/361 |
| 3,865,751 A | 2/1975 | Banks et al. ............... 502/251 |
| 3,865,800 A | 2/1975 | Weitz et al. ............... 526/157 |
| 3,944,533 A | 3/1976 | Beck et al. ................ 526/84 |
| 4,232,180 A | * 11/1980 | Kelly ....................... 585/645 |
| 4,654,461 A | 3/1987 | Drake et al. ............... 585/600 |
| 4,707,465 A | 11/1987 | Kukes ....................... 502/219 |
| 4,837,358 A | 6/1989 | Byers et al. ............... 560/261 |
| 4,950,826 A | 8/1990 | Zerpner et al. ............. 585/353 |
| 5,698,760 A | 12/1997 | Kelly ....................... 585/643 |
| 5,877,365 A | 3/1999 | Chodorge et al. ........... 585/329 |

FOREIGN PATENT DOCUMENTS

| | | |
|---|---|---|
| DE | 2051798 | 10/1970 |
| DE | 2051799 | 10/1970 |
| DE | 2424298 | 5/1974 |
| GB | 1163657 | * 9/1969 |
| JP | 8-176022 | * 9/1969 |

OTHER PUBLICATIONS

Grubbs, *Prog. in Inorg. Chem.*, vol. 24, p. 1–50, 1978.
Grubbs, *Comp. Org. Chem.*, 1982, vol. 8, p. 499–551.
Grubbs et al, *Science*, 1989, vol. 243, pp. 907–915.
Breslow, *Prog. Polym. Sci.*, vol. 18, 1993, pp. 1141–1195.
Hoecker et al., *Adv. Mater.*, vol. 6, No. 1, 1994, pp. 21–36.
Sundararajan, *J. of Sci. & Indus. Res.*, vol. 53, Jun. 1994, pp. 418–432.
Schrock, *Acc. Chem. Res.*, 1990, vol. 23, pp. 158–165.
Banks et al., *J. of Mol. Cat.*, vol. 15, 1982, pp. 21–33.
Banks, *J. of Mol. Cat.*, vol. 8, 1980, p. 269–276.
Zuech et al., *J. of Amer. Chem. Soc.*, 92:3, 1970, pp. 528–531.
Pinazzi et al., *C.R. Acad. Sci.*, Series C, 1973, pp. 1077–1079.
*Chem. Abst.*, vol. 78, No. 26, Jul. 2, 1973, AN 160135m.
*Chem. Abst.* 3306t (Abst. of HERRISSON, *Makromol. Chem.*).
Lal et al., *J. Org. Chem.*, vol. 40, No. 6, 1975, pp. 775–779.
Lal et al., *Polym. Prep.* (Am. chem. Soc., Div. Polym. Chem.) 13, 1972, pp. 914–919.

\* cited by examiner

*Primary Examiner*—Thuan D. Dang
(74) *Attorney, Agent, or Firm*—Keil & Weinkauf

(57) ABSTRACT

A process for preparing cyclopentene oligomer mixtures of the formula I

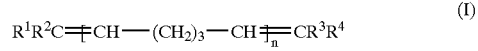

comprises reacting in a homogeneously or heterogeneously catalyzed metathesis reaction a hydrocarbon mixture which contains cyclopentene and acyclic monoolefins and which originates from petroleum processing by cracking ($C_5$ fraction);
cyclopentene oligomers of the formula I obtainable by this process and their use are also described.

15 Claims, No Drawings

OLIGOMER MIXTURES DERIVED FROM CYCLOPENTENE; METHOD FOR THE PRODUCTION AND USE THEREOF

BACKGROUND OF THE INVENTION

1. Field of the Invention

The present invention relates to cyclopentene-derived oligomer mixtures, a process for their preparation by ring-scission metathesis and their use as intermediates for further processing by double-bond functionalization.

2. Description of the Related Art

In the processing of petroleum by steam crackers, a hydrocarbon mixture termed $C_5$ fraction is, produced, inter alia, which has a high total olefin content of, for example, about 50%, of which approximately 15% is made up of cyclopentene and the remainder of acyclic monoolefins, especially n-pentene (approximately 15% by weight) and other isomeric pentenes (approximately 20% by weight). This mixture can, if desired, prior to further processing, be subjected to a catalytic partial hydrogenation, so that dienes are then essentially no longer present. To isolate the cyclopentane which is present at about 8% in the $C_5$ fraction and is used for example as propellant as substitute for the CFCs and HCFCs which are of concern with regard to harm to the atmosphere, and, if appropriate, to isolate the remaining saturated acyclic pentenes, it is necessary according to the prior art to subject the $C_5$ fraction to work-up by distillation. This is highly complex in processing terms if acyclic and cyclic $C_5$ olefins, in particular cyclopentene, are simultaneously present. There is therefore a requirement for a process for removal of the cyclopentene other than by distillation, with or without other monoolefins, from the $C_5$ fraction, as far as possible with simultaneous production of a new product of value.

An industrially important olefin reaction which retains the number of C=C double bonds is metathesis. The term metathesis formally denotes the exchange of alkylidene groups between two alkenes in the presence of homogeneous or heterogeneous transition metal catalysts. A simple example of an industrially used metathesis reaction between two acyclic olefins is the conversion of propene to ethene and 2-butene.

The ring-scission polymerization of cyclic olefins, which proceeds by the metathesis mechanism, leads to poly-(1-alkenylenes), which are termed polyalkenamers. In contrast to the polymerization of vinyl compounds, in this case the double bonds of the monomer are retained in the polymer. The metathesis of acyclic and cyclic olefins is described, for example, by R. H. Grubbs in Progress in Inorganic Chemistry, John Wiley & Sons, New York, 1978, Vol. 24, pp 1–50; in Comprehensive Organomet. Chem., Pergamon Press, Ltd., New York, 1982, Vol. 8, pp. 499–551 and in Science (1989) 243, pp 907–915; and by D. S. Breslow in Prog. Polym. Sci. Vol. 18 (1993) pp. 1141–1195; by H. Höcker and H. Keul in Adv. Mater. 6 (1994) No. 1, pp. 21–36 and by G. Sundararajan in J. Sci. Indus. Res. Vol. 53 (1994) pp. 418–432.

R. R. Schrock, in Acc. Chem. Res. 23 (1990) pp. 158 ff., describes the mechanism of the ring-scission metathesis polymerization in accordance with the following scheme:

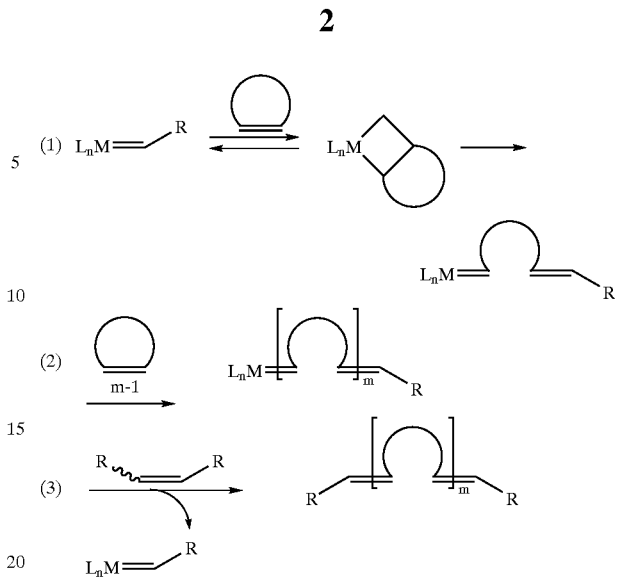

In this scheme, in the initiation step (1), a cycloolefin is first added to a metal carbene complex, with formation of a metallacyclobutane intermediate, which can either break down to reform starting materials, or can open to give a new carbene complex with chain elongation. The chain growth (propagation) (2) proceeds in the ideal case of the living ring-scission metathesis polymerization in such a manner that one polymer strand is formed per metal center, so that monodisperse polymers having a polydispersity of almost 1 are obtained. The chain termination (3), ie. the detachment of the polymer from the metal, is generally carried out by adding an acyclic olefin. Here, in the ideal case, it is possible both to exert a targeted influence on the chain length and to regenerate the catalyst. In the case of chain termination using a functionalized olefin, the functionality transfers to the end of the polymer chain.

BE-A-759774 describes a process for controlling the molar mass and molar mass distribution in ring-scission metathesis polymerization, in which, for example when a polyoctenamer is prepared, 1-pentene is used as acyclic olefin and thus chain-termination reagent.

By using acyclic olefins, firstly, the chain length may be controlled specifically in the ring-scission metathesis polymerization. Secondly, the ethenolysis of cyclic olefins, in which equimolar amounts of a cyclic olefin are reacted with ethene according to the following scheme:

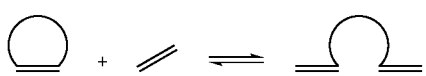

serves in the preparation of α,ω-unsaturated olefins which are otherwise difficult to synthesize.

U.S. Pat. No. 3,715,410 describes reacting cyclic olefins with acyclic olefins to give acyclic polyenes in the presence of what is termed an olefin disproportionation catalyst. Thus, by reacting cyclic monoolefins or non-conjugated polyolefins with ethene α,ω-unsaturated acyclic diolefins or polyenes may be prepared. α,ω-unsaturated diolefins can readily be converted to diols having terminal hydroxyls, and are used in the preparation of polyesters, for example. By reacting cyclic monoolefins with a substituted acyclic olefin, non-conjugated acyclic diolefins having one terminal double bond and one terminally substituted double bond are obtained, for example when cyclooctene is reacted with propene to give 1,9-undecadiene. These are used, for example, as monomers in homopolymerization or copolymerization in order to obtain polymers which may be readily crosslinked.

DE-A-2 047 270 describes a process for preparing a catalyst for the disproportionation of olefins based on organometallic compounds which contain a transition metal of subgroup 6 and a metal of main groups 1 to 3 of the Periodic Table of the Elements, preferably aluminum. The catalysts are suitable both for homo- and cross-disproportionations, in which a mixture of two different olefins is reacted with formation of a product mixture according to the following general scheme:

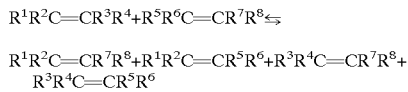

The disproportionation reactions described include:
1. The conversion of a mixture of one acyclic mono- or polyolefin and one cyclic mono- or polyolefin to an acyclic polyolefin of higher molecular weight.
2. The conversion of one or more cyclic mono- or polyolefins with formation of cyclic polyolefins of higher molecular weight.
3. The conversion of one or more acyclic polyolefin with formation of cyclic mono- or polyolefins and acyclic mono-or polyolefins.

DE-A-2 028 935 describes polyalkenamers, which are prepared by ring-scission metathesis polymerization from cyclic olefins and unsaturated esters having double bonds which are not situated in a ring, a catalyst system consisting of a tungsten compound or molybdenum compound and an organoaluminum compound as well as a compound which contains one or more hydroxyls and/or sulfhydryls being used.

DE-A-2 051 798 also describes a process for preparing polyalkenamers by ring-scission polymerization of cyclic olefins by means of catalyst consisting of:
a) Tungsten halides or tungsten oxyhalides containing hexavalent tungsten,
b) an organoaluminum compound,
c) a monocarboxylic acid soluble in the reaction mixture.

DE-A-2 051 799 also describes a process for preparing polyalkenamers by ring-scission polymerization of cyclic olefins using a catalyst system based on a hexavalent tungsten compound and an organoaluminum compound.

DE-A-3 529 996 describes a process for preparing polyalkenamers having an elevated cis content of the double bonds present in the polymer, prepared by ring-scission metathesis polymerization of cis,cis-cycloocta-1,5-diene or norbornene, the polymerization being carried out in the presence of an open-chain 1,3-diene, such as isoprene, or a cyclic 1,3-diene, such as cyclohlexa-1,3-diene.

DE-A-2 201 161 describes a process for preparing polymers from cycloolefins, preferably cyclopentene and cyclooctene, by ring-scission metathesis polymerization using a catalyst system consisting of a transition metal salt, preferably an (oxy)halide of chromium, molybdenum or tungsten, an organometallic compound of an element of main group 4, preferably an alkyl or aryl compound of tin or of lead, and an aluminum halide.

DE-A-2 343 093 describes a process for the ring-scission polymerization of cyclic olefins on catalysts consisting of
a) a halide of a metal from groups Vb or VIb of the Periodic Table of the Elements,
b) an organometallic compound of a metal of groups IIa, IIIa and IVa of the Periodic Table of the Elements,
c) with or without a cocatalyst which contains a C=C double bond conjugated with a C=O double bond, for example an α,β-unsaturated aliphatic monocarboxylic or polycarboxylic acid. This process produces polyalkenamers which have relatively high values of polydispersity and thus a broad molecular weight distribution.

DE-A-2 424 298 describes a process for preparing segment polymers by ring-scission metathesis polymerization of a cycloolefin with a high molecular weight oligoolefin, preferably an α,ω-diolefin having additional side-chain double bonds. This produces polymers having tailor-made product properties.

Of the metathesis processes mentioned above, the synthesis of olefins, diolefins and specially functionalized olefins which are not readily accessible conventionally has primarily found wide industrial application. J. Mol. Catal. (1982) 15, pp 21 ff. describes the olefin metathesis process developed and utilized industrially by the Phillips Petroleum Company. A distinction is made here between processes for preparing monoolefins, which include, for example, the triolefin process for preparing high-purity ethylene and linear butenes from propene and the neohexene process for cleaving diisobutylene with ethylene to prepare neohexene (3,3-dimethyl-1-butene) and isobutylene, and processes for preparing α,ω-unsaturated di- and polyenes by the ethenolysis of cyclic olefins described above. To prepare functionally substituted olefins, special metathesis catalysts are required which are not poisoned by polar substituents. These are based on heteroatom-substituted carbene complexes, as initially prepared by E. O. Fischer, which are activated by metal (oxy)halides. A highly active cocatalyst composition is obtained by combining tin(IV) chloride with silicon tetrachloride or germanium tetrachloride, for example.

R. L. Banks, in J. Mol. Catal. (1980) 8, pp. 269 ff., likewise describes industrial aspects of olefin disproportionation reactions.

U.S. Pat. No. 3,652,703 describes a process for olefin metathesis using a catalyst based on ruthenium on a silicon dioxide support.

U.S. Pat. No. 3,659,008 describes a process for preparing non-conjugated acyclic polyenes having 4 carbons between the double bonds, comprising the disproportionation of ethylene and a cyclic polyene containing 4 carbons between the double bonds, such as 1,5-cyclooctadiene, a mixture of desired acyclic polyenes as well as denser and lighter secondary polyenes being obtained.

U.S. Pat. No. 3,660,507 describes a process for the metathesis of olefin mixtures of acyclic and/or cyclic olefins on a catalyst system comprising an active catalyst composition and magnesium oxide.

U.S. Pat. No. 3,792,102 likewise describes the use of a magnesium oxide layer in a layered-bed catalyst for the disproportionation of mixtures of acyclic and cyclic olefins for preparing dienes.

U.S. Pat. No. 3,865,751 likewise describes an active catalyst composition for converting olefins, comprising a mixture of magnesium oxide and an olefin disproportionation catalyst.

U.S. Pat. No. 3,836,480 describes an active catalyst composition for converting olefins, comprising a disproportionation catalyst and magnesium oxide which was treated with carbon monoxide, nitrogen monoxide or hydrogen.

U.S. Pat. No. 4,707,465 describes an improved olefin disproportionation catalyst prepared by mixing a high-melting inorganic oxide which contains a catalytically active amount of molybdenum oxide or tungsten oxide with an alkali metal dithionite salt or alkaline earth metal dithionite salt as promotor.

U.S. Pat. No. 3,637,893 describes a process for disproportionating two non-conjugated olefins on a disproportionation catalyst consisting of a perchlorinated hydrocarbon and a high-melting inorganic oxide which contains at least 0.1% by weight of molybdenum oxide or tungsten oxide.

U.S. Pat. No. 3,691,095 describes a process for preparing catalysts for olefin disproportionation reactions by reacting a transition metal carbonyl complex of the formula $A_n(MM'(CO)_qL_m)^{-n}$, where A is an alkali metal cation or an ammonium, phosphonium or arsonium cation, M is a metal of subgroup 6, M' is a metal of subgroup 7 or 8, L is a monodentate or bidentate ligand, such as CO, $NH_3$, hydrazine, etc., with an ammonium, phosphonium or arsonium halide and an organometallic activator which includes an organoaluminum halide.

J. Am. Chem. Soc. 92 (1970) pp. 528 ff. describes homogeneous catalysts for olefin disproportionation reactions based on nitrosyl molybdenum and tungsten compounds. The catalysts are produced by reacting nitrosyl molybdenum and nitrosyl tungsten derivatives with organoaluminum compounds, such as $C_2H_5AlCl_2$ and $(CH_3)_3Al_2Cl_3$ and are suitable for most of the abovementioned olefin metathesis reactions.

A further important industrial metathesis reaction is cross metathesis which, as mentioned above, is described, for example, in BE-A-759 774. C.R. Acad. Sc., Ser. C (1973) pp. 1077 ff. describes the metathesis between cycloocta-1, 5-diene and 4-octene using a $WCl_6/EtAlCl_2/EtOH$ catalyst system, polybuta-1,4-dienes ultimately being obtained by cross metathesis between one acyclic and one cyclic monomer or oligomer in each case.

U.S. Pat. No. 3,622,644 describes a process for preparing oligomers from ethene And a cyclic monoolefin, preferably cyclopentene, using a catalyst which comprises a) a rhenium complex of the formula $(L)_2ReOX_3$, where X is halogen and L is a ligand derived from trivalent phosphorus, arsenic or antimony and b) an organoaluminum compound.

U.S. Pat. No. 4,654,461 describes a process for preparing 1,5,9-tetradecatriene having a high cis content by disproportionating 1,5-cyclooctadiene and 1-hexene in the presence of a heterogeneous catalyst based on molybdenum oxide on a silicon dioxide support having a high surface area. Only the simplest cross metathesis product, which was obtained in a yield of only 9%, is in the area of interest of the present publication.

EP-B-0 235 742 describes a process for preparing 9-alkenyl esters, the cross metathesis product of cyclooctene and an α-olefin having 3 to 12 carbon atoms, a 1,9-alkadiene, being prepared in a first reaction step. In this process, the catalyst is selected from the group consisting of silicon dioxide, aluminum oxide, aluminum phosphate, zirconium phosphate, calcium phosphate, magnesium phosphate, titanium phosphate or thorium oxide, which contain a promotor.

Makromol. Chem. 141 (1970) pp. 161 ff. describes the telomerization of cyclic olefins with acyclic olefins in the presence of $WOCl_4/Al(C_2H_5)_2Cl$ or $WOCl_4/Sn(C_4H_9)_4$ as catalyst. The term telomerization is applied to a polymerization in which a molecule AB, which is termed the telogen is reacted with n-molecules of a monomer M, which is termed the taxogen, to give an oligomer or polymer $A(M)_nB$, which is termed the telomer. At the ends of the telomers obtained by metathesis are situated two identical or different groups which have formed from the acyclic olefin by a non-continuing reaction. The chain termination reaction, with formation of the telomers, can be considered as a cross metathesis. The telomer distribution obeys a statistical law and agrees with the following reaction scheme, comprising a) the disproportionation of acyclic olefins, b) the polymerization of cyclic olefins and c) the telomerization of cyclic olefins with acyclic olefins.

The postulated mechanism is studied with various telomerizations, for example that of cyclopentene and 2-pentene, the experimental product distributions being compared with the calculated ones (assuming the above mechanism). On the basis of the good agreement obtained, the assumed mechanism appears to be realistic. In the telomerization of cyclopentene and 2-pentene, only a relative oligomer content of about 30 mol % or less was obtained with the two catalyst systems used. This excludes the method described for industrial preparation of $C_5$ oligomer mixtures. There is no reference to a possible use of $C_5$ olefin mixtures from petroleum refining fractions as starting material mixtures.

J. Lal, R. R. Smith and J. M. O'Connor, in Polym. Prepr. (Am. Chem. Soc., Div. Polym. Chem.) 13 (1972) 2, pp. 914 ff., describe a process for preparing polyenes by cross metathesis of a cyclomonoolefin, such as cyclooctene, or of a non-conjugated cyclodiene with an a-olefin, such as 1-hexene on a $WCl_6/EtAlCl_2/EtOH$ catalyst at ambient temperature and with reaction times from about 1 to 2 hours. Gas-chromatographic analysis of the cross metathesis products showed a product maximum at a carbon number of 14. The resulting cross metathesis products, to increase the molar mass, were then subjected to a copolymerization with the α-olefin previously used.

J. Org. Chem. 40 (1975) pp. 775 ff. describes the metathesis of 1-hexene and cyclooctene. Three different homologous product series of linear non-conjugated polyenes are obtained, depending on the primary metathesis products. Series A are secondary products of 1,9-decadiene of the formula

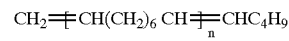

having one terminal and one internal terminating double bond. They originate from a cross metathesis between hexene and cyclooctene. Series B are secondary products of 5-decene of the formula

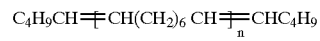

having two internal terminating double bonds. They originate from a hexane self-metathesis, with formation of 5-decene and ethene. Series C are secondary products of 1,9-tetradecadiene of the formula

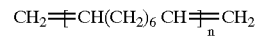

having two terminal terminating double bonds. They originate from a cross metathesis between cyclooctene and the ethene formed in series B. The main product of the reaction was $C_{14}H_{26}$ (1,9-tetradecadiene) from the cross metathesis of 1-hexene and cyclooctene, with a total content of 40% by weight. However, other reaction products from all three of the abovementioned series could be detected with higher molecular weights, where the total cycloolefin conversion was greater than 70%. The catalysts used were derived from $WCl_6$ and an organometallic compound, preferably $WCl_6/EtAlCl_2/EtOH$ and $WCl_6/Bu_4Sn/2Et_2O$.

U.S. Pat. No. 3,527,828 describes a process for preparing hydrocarbon telomers (polyenes) by reacting an acyclic monoolefin with a monocyclic or polycyclic olefin, which contains up to 4 condensed rings and up to 4 non-conjugated double bonds, on a heterogeneous molybdenum oxide or rhenium oxide catalyst. As examples of metathesis, the following pairs of starting materials of cyclic olefin (taxogen) and acyclic olefin (telogen) were reacted, the corresponding polyenes (telomers) being obtained:

a) cyclopentene and ethylene gave as main products 1,6,11-dodecatriene (18.7% selectivity) and 1,6,11,16-heptadecatetraene (5.5% selectivity) at 35.6% cyclopentene conversion;

b) cyclopentene and 1,6-heptadiene produced as main products 1,6,11-dodecatriene (selectivity 51%) and 1,6,11,17-octadecatetraene (selectivity 35%) at a cyclopentene conversion of 12%;

c) cyclooctene and ethylene produced as main products 1,9-decadiene, 1,9,17-octadecatriene and 1,9,17,25-hexacosatetraene, the cyclooctene conversion rate being between 25 and 71%, as a function of the reaction temperature;

d) norbornene and ethylene predominantly produced $C_{16}$, $C_{23}$ and $C_{30}$ telomers at a norbornene conversion rate of 62%.

In this publication, and in none of the other previously mentioned publications, there is a reference to possible use of $C_5$ olefin mixtures from petroleum refining for preparing oligomers (telomers).

EP-A-691 318 describes a process for preparing a $C_4$ olefin mixture which predominantly contains isobutene and 1-butene, as well as propene. In this process, an olefin-containing $C_5$ hydrocarbon mixture, for example produced in the stream cracking of naphtha, is initially subjected to a hydrogenation with subsequent fractionation and is then reacted with ethene in a metathesis reaction. The metathesis catalysts used in this process are exclusively heterogeneous rhenium oxide, tungsten oxide, molybdenum oxide and cobalt oxide catalysts. The object underlying the publication is to provide a process for preparing isomeric butenes, that is olefins having a molecular weight lower than those present in the starting hydrocarbon mixture ($C_5$ fraction). To achieve this object, the metathesis reaction is performed in the presence of an up to 10-fold molar excess of ethene, the undesirable self-metathesis of the $C_5$ fraction being suppressed in this process. There is no reference in the publication to the possibility of utilizing the self-metathesis for oligomerizing the cyclic and acyclic olefins present in the $C_5$ fraction, in the context of a ring-scission metathesis polymerization.

SUMMARY OF THE INVENTION

It is an object of the present invention to provide a process for processing a $C_5$ mixture from petroleum refining ($C_5$ fraction) which, in addition to saturated hydrocarbons, further contains cyclic and acyclic monoolefins, where the olefins, as far as possible with conversion into a product of value, are to be separated off from the acyclic hydrocarbons. Advantageously in this case the product of value has a higher molecular weight than the olefins.

We have found that this object is achieved, surprisingly, by a process for preparing oligomer mixtures derived from cyclopentene, the $C_5$ fraction being subjected to a metathesis reaction. The novel oligomers prepared according to the invention are suitable, for example, as intermediates for end products obtainable by functionalizing the double bonds in the context of a polymer-like reaction.

The present invention thus relates to a process for preparing cyclopentene-derived oligomer mixtures of the formula I

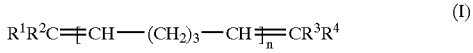

where n is an integer from 1 to 15, $R^1$, $R^2$, $R^3$, $R^4$ independently of one another are hydrogen or alkyl, which comprises reacting, in a homogeneously or heterogeneously catalyzed metathesis reaction, a hydrocarbon mixture which contains cyclopentene and acyclic monoolefins and originates from petroleum refining by cracking ($C_5$ fraction).

DETAILED DESCRIPTION OF THE INVENTION

The value n in formula I is the number of cyclopentene units introduced into the cyclopentene-derived oligomers by ring-scission metathesis reaction. Preferably, the process according to the invention produces oligomer mixtures in which a very large proportion, for example at least 40% by weight (determined by integrating the area of the gas chromatograms; instrument: Hewlett Packard; detector: flame ionization detector; column: DB 5.30 m×0.32 mm, coating 1 $\mu$; temperature program: 60° C. 5 min, isothermal, heating rate 10° C./min max: 300° C.), have a value of n>1. The value n and thus the degree of the ring-scission metathesis can, as explained below, be influenced by the activity of the metathesis catalyst used.

The radicals $R^1$, $R^2$, $R^3$ and $R^4$ are independently of one another hydrogen or alkyl, where the expression "alkyl" includes straight-chain and branched alkyl groups.

Preferably, these are straight-chain or branched $C_1$–$C_{15}$-alkyl, preferably $C_1$–$C_{10}$-alkyl, in particular preferably $C_1$–$C_5$-alkyl. Examples of alkyl groups are, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl, etc.

The degree of branching and the number of carbons of the terminating alkyl radicals $R^1$, $R^2$, $R^3$ and $R^4$ depend on the structure of the acyclic monoolefins of the hydrocarbon mixture used and on the activity of the catalyst. As described below more precisely, the activity of the catalyst influences the degree of cross metathesis (self-metathesis) of the acyclic olefins with the formation of structurally novel olefins into which cyclopentene is then formally inserted in the context of ring-scission metathesis polymerization.

Preferably, by seans of the process according to the invention, oligomer mixtures are prepared which hive an elevated proportion of oligomers having only one terminal double bond.

The metathesis reaction formally includes
a) the disproportionation of the acyclic monoolefins of the hydrocarbon mixture by cross metathesis,
b) the oligomerization of the cyclopentene by ring-scission metathesis,
c) chain termination by reacting the oligomers from b) with an acyclic olefin of the hydrocarbon mixture or of a product from a), where the steps a) and/or b) and/or c) can proceed repeatedly, alone or in combination.

Step a)

The cross metathesis of the acyclic monoolefins shall be described with the example of the metathesis of 1-pentene and 2-pentene:

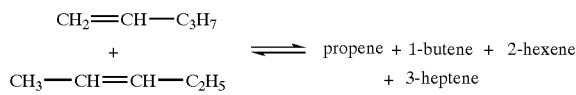

By combinations of cross metathesis of different acyclic olefins and self-metathesis of identical acyclic olefins, such as the self-metathesis of 1-pentene to give ethene and 4-octene, and by repeated passage through this reaction, a multiplicity of monoolefins having different structures and carbon numbers are obtained which form the end groups of the oligomers according to the invention. The content of cross metathesis products which increases with increasing activity of the catalyst used also influences the double bond content of the oligomers. Thus, in the case of the self-metathesis of 1-pentene described above, ethene is released which can escape, if appropriate, in the gaseous form, one double bond equivalent being removed from the reaction. At the same time, the content of oligomers without terminal double bonds increases. Thus, in the above example, an oligomer without terminal double bonds is formed, for example by insertion of cyclopentene into 4-octene.

Step b)

The mean number of cyclopentene insertions into the growing chain in the context of a ring-scission metathesis polymerization determines the mean molecular weight of the cyclopentene oligomer mixture formed. Preferably, the process according to the invention forms oligomer mixtures having a mean molecular weight of at least 274 g per mole, which corresponds to a mean number of three cyclopentene units per oligomer.

Step c)

The chain termination is performed by reacting an oligomer, which still has one active chain end in the form of a catalyst complex (alkylidene complex), with an acyclic olefin, an active catalyst complex being recovered in the ideal case. The acyclic olefin may originate unchanged from the hydrocarbon mixture originally used for the reaction or may have been previously modified in a cross metathesis according to stage a).

The process according to the invention is suitable quite generally for preparing oligomers from hydrocarbon mixtures which contain acyclic and cyclic olefins.

Preferably, a hydrocarbon mixture arising on an industrial scale in petroleum refining is used which, if desired, can be subjected in advance to a catalytic partial hydrogenation to remove dienes. A mixture which is particularly suitable for use in the present process is, for example, a mixture enriched in saturated and unsaturated $C_5$ hydrocarbons ($C_5$ fraction). To obtain the $C_5$ fraction, pyrolysis gasoline produced in the steam cracking of naphtha may, for example, be first subjected to a selective hydrogenation in order to convert selectively the dienes and acetylenes present into the corresponding alkanes and alkenes and may then be subjected to fractional distillation, with on the one hand the $C_6$–$C_8$ fraction which is of importance for further chemical syntheses and contains the aromatic hydrocarbons being produced, and on the other, the $C_5$ fraction used for the process according to the invention being produced.

The $C_5$ fraction generally has a total olefin content of at least 30% by weight, preferably at least 40% by weight, in particular at least 50% by weight.

Suitable $C_5$ hydrocarbon mixtures are those having a total cyclopentene content of at least 5% by weight, preferably at least 10% by weight, in particular at least 12% by weight, and generally not more than 30% by weight, preferably not more than 20% by weight.

Furthermore, suitable $C_5$ hydrocarbon mixtures have a content of pentene isomers in the acyclic monoolefins of at least 70% by weight, preferably at least 80% by weight, in particular at least 90% by weight.

According to a preferred embodiment of the process according to the invention, a $C_5$ fraction which is produced on an industrial scale is used which has a total olefin content of, for example, from 50 to 60% by weight, such as about 56%, a cyclopentene content of, for example, from 10 to 20% by weight, such as about 15% by weight and a content of pentene isomers of, for example from 33 to 43% by weight, such as about 38% by weight, about 16% by weight being due to the n-pentene and about 22% by weight to isomeric pentenes.

According to a specific embodiment of the process according to the invention, a hydrocarbon mixture is used which comprises the $C_5$ fraction and a petroleum fraction containing acyclic $C_4$ olefins (raffinate 2).

According to a further specific embodiment of the process according to the invention, a hydrocarbon mixture is used which comprises the $C_5$ fraction and ethene. In this case, oligomer mixtures having an elevated double bond content are obtained. On the one hand, this is achieved by ethenolysis of the acyclic n- and isopentenes present in the $C_5$ fraction to give shorter-chain α-olefins, such as propene and 1-butene, which react with cyclopentene in a ring-scission metathesis reaction with formation of oligomers each of which have a terminal double bond. In the presence of ethene, the self-metathesis of the acyclic olefins with formation of further ethene, such as the selfmetathesis of 1-pentene to form ethene and 4-octene, which leads, as chain termination reagent, to products without terminal double bonds, is suppressed. On the other hand, a further increase in the double bond content is achieved due to the ethenolysis of cyclopentene with ethene to give 1,6-heptadiene. This forms series of oligomers each of which have two terminal double bonds. Preferably, oligomer mixtures having increased density of functionality result from the use of the oligomer mixtures having increased double bond content for functionalization thus obtained.

Suitable catalysts for the metathesis are known from the prior art and include homogeneous and heterogeneous catalyst systems. The catalyst systems previously described as prior art are expressly incorporated by reference. Generally, the catalysts suitable for the process according to the invention are based on a transition metal of subgroup 6, 7 or 8 of the Periodic Table of the Elements, catalysts based on Mo, W, Re and Ru preferably being used.

Suitable homogeneous catalyst systems are generally transition metal compounds which, in combination or not with a cocatalyst and/or in the presence or absence of the olefin starting materials, are capable of forming a catalytically active metal carbene complex. Systems of this type are described, for example, by R. H. Grubbs in Comprehensive Organomet. Chem., Pergamon Press, Ltd., New York, Vol. 8, (1982) pp. 499 ff.

Suitable catalyst/cocatalyst systems based on W, Mo and Re can, for example, comprise at least one soluble transition metal compound and one alkylating agent. These include, for example, $MOCl_2(NO)_2(PR_3)_2/Al_2(CH_3)_3Cl_3$; $WCl_6/BuLi$; $WCl_6/EtAlCl_2(Sn(CH_3)_4)/EtOH$; $WOCl_4/Sn(CH_3)_4$; $WOCl_2(O-[2,6-Br_2-C_6H_3])/Sn(CH_3)_4$; $CH_3ReO_3/C_2H_5AlCl_2$, the four last-mentioned systems being preferred for the process according to the invention.

Further transition metal-alkylidene complexes suitable as metathesis catalysts are described by R. R. Schrock in Acc. Chem. Res., 23 (1990) pp. 158 ff. Generally, these are tetracoordinate Mo- and W-alkylidene complexes which additionally have two bulky alkoxy ligands and one imido ligand. Preferably $((CH_3)_3CO)_2Mo(=N-[2,6-(i-C_3H_7)_2-C_6H_3])$ $(=CHC(CH_3)_2C_6H_5)$ and $[(CF_3)_2C(CH_3)O]_2Mo(=N-[2,5-(i-C_3H_7)-C_6H_3])(=CH(CH_3)_2C_6H_5)$ are used for the process according to the invention.

Particularly preferably, the homogeneous metathesis catalysts used are the catalysts which are described in Angew. Chem. 107 (1995) pp. 2179 ff., in J. Am. Chem. Soc. 118 (1996) pp. 100 ff. and in J. Chem. Soc., Chem. Commun., (1995) pp. 1127 ff. These include, in particular, $RuCl_2(=CHR)(PR'_3)_2$, preferably $RuCl_2(=CHC_6H_5)(P(C_6H_{11})_3)_2$, $(\eta^6\text{-p-cymene})RuCl_2(P(C_6H_{11})_3)/(CH_3)_3SiCHN_2$ and $(\eta^6\text{-p-cymene})RuCl_2(P(C_6H_{11})_3)/C_6H_5CHN_2$. The latter two are produced in situ from 1 mol equivalent of $(\eta^6\text{-p-cymene})RuCl_2(P(C_6H_{11})_3)$ and 3 mol equivalents of diazoalkane $((CH_3)_3SiCHN_2$ or $C_6H_5CHN_2)$.

Suitable heterogeneous catalyst systems generally comprise a transition metal compound on an inert support which is capable, without cocatalyst, of forming a catalytically active alkylidene complex by reaction with the olefin starting materials. In the process according to the invention, $Re_2O_7$ and $CH_3ReO_3$ are preferably used.

Suitable inorganic supports are the oxides customary for this, in particular silicon oxides and aluminum oxides, aluminosilicates, zeolites, carbides, nitrides, etc. and mixtures of these. Preferably, the supports used are $Al_2O_3$, $SiO_2$ and their mixtures, in combination or not with $B_2O_3$ and $Fe_2O_3$.

The abovementioned homogeneous and heterogeneous catalyst systems differ very greatly in their catalytic activity, so that the individual catalysts have different optimum reaction conditions for the metathesis. As already described above, the catalytic activity with respect to cross metathesis (step a)) also influences the product distribution of the oligomer mixtures of the formula I derived from cyclopentene. Thus the ruthenium-based homogeneous catalyst systems $RuCl_2(=CHC_6H_5)$ $(P(C_6H_{11})_3)_2$, $(\eta^6\text{-p-cymene})RuCl_2(P(C_6H_{11})_3)/(CH_3)_3SiCHN_2$ and $(\eta^6\text{-p-cymene})RuCl_2(P(C_6H_{11})_3)/C_6H_5CHN_2$ are particularly suitable for the process according to the invention. The first-mentioned ruthenium complex has a higher catalytic activity then the two last-mentioned, which, with reaction conditions otherwise identical, leads to higher space-time yields. However, at the same time, with the first complex the cross metathesis occurs to an increased extent, some ethene also being released and thus the cyclopentene-derived oligomer mixture obtained has a somewhat lower double bond content, which is expressed as a lower iodine number, for example. In addition, owing to the cross metathesis, a greater number of acyclic olefins without terminating double bonds are available, so that, using the first-mentioned homogeneous ruthenium catalyst, cyclopentene-derived oligomers of the formula I which have only one terminal double bond or none at all, are obtained to an increased extent. The two last-mentioned ruthenium complexes have a somewhat lower catalytic activity than the first-mentioned, so that using them in the process according to the invention, cyclopentene-derived oligomer mixtures of the formula I are obtained which have a higher double bond content and thus a higher iodine number as well as a greater number of terminal double bonds.

The heterogeneous catalyst systems also have the above-described differences in activity together with the corresponding effects on the metathesis products. If $CH_3ReO_3$ on $Al_2O_3$ is used as heterogeneous catalyst for the process according to the invention, this catalyst has a higher catalytic activity than the corresponding homogeneous catalyst system of $CH_3ReO_3/(C_2H_5)AlCl_2$.

Advantageously, the heterogeneous catalyst used is $Re_2O_7$ on $Al_2O_3$. This has an activity roughly comparable with $RuCl_2(=CHC_6H_5)(P(C_6H_{11})_3)_2$, as well as a similar product distribution and can be reused, after regeneration in an air stream at elevated temperatures, such as about 550° C.

If desired, depending on the catalyst used, cyclopentene-derived oligomer mixtures having variable double bond contents and variable contents of terminal double bonds can thus be obtained.

According to a particularly preferred embodiment of the process according to the invention, the metathesis catalyst used is a homogeneous ruthenium-based catalyst selected from the group consisting of $RuCl_2(=CHC_6H_5)(P(C_6H_{11})_3)_2$, $(\eta^6\text{-p-cymene})RuCl_2(P(C_6H_{11})_3)/(CH_3)_3SiCHN_2$ and $(\eta^6\text{-p-cymene})RuCl_2(P(C_6H_{11})_3)/C_6H_5CHN_2$, which is added to the reaction mixture as a solution in an organic solvent. Suitable solvents are, for example, aromatic hydrocarbons, such as toluene and xylene, as well as halogenated alkanes, such as $CH_2Cl_2$, $CHCl_3$, etc.

The reaction temperature in the case of reactive catalyst systems is from −20 to 200° C., preferably from 0 to 100° C., in particular from 20 to 80° C.

The reaction can be carried out at an elevated pressure of up to 5 bar, preferably up to 2 bar, or, particularly preferably, at ambient pressure.

According to a further particularly preferred embodiment of the process according to the invention, the metathesis catalyst used is a rhenium-based heterogeneous catalyst selected from among $CH_3ReO_3/Al_2O_3$ and preferably $Re_2O_7/Al_2O_3$, which is added to the reaction mixture without addition of solvent.

The reaction temperature when these catalysts, which are somewhat less active in comparison with the abovementioned homogeneous catalyst systems, are used is from about 20 to 120° C., preferably from 30 to 100° C., in particular from 40 to 80° C.

The reaction is preferably carried out at an elevated pressure of from 2 to 20 bar, preferably from 3 to 15 bar, in particular from 4 to 12 bar.

The equipment for the process according to the invention can be designed for either continuous or batchwise processes. Suitable reaction apparatuses are known to those skilled in the art and are described, for example, in Ullmanns Enzyklopädie der technischen Chemie [Ullmanns Encyclopedia of Industrial Chemistry], Vol. 1 (1951) pp. 743 ff. These include, for the batchwise process, stirred tanks, for example, and, for the continuous process, tubular reactors, for example.

According to a suitable batchwise variant of the process according to the invention, the $C_5$ fraction, for example, can be reacted on one of the homogeneous ruthenium catalysts which have been described above as preferred and which is generated if desired in situ in the reactor vessel, to give cyclopentene-derived oligomer mixtures of the formula I in a metathesis reaction.

According to a further suitable continuous variant of the process according to the invention, the $C_5$ fraction, for example, can be reacted in a tubular reactor on one of the heterogeneous rhenium catalysts described above as preferred.

Space-time yields of at least 10 g $l^{-1}$ $h^{-1}$, preferably at least 15 g $l^{-1}$ $h^{-1}$ are achieved with both possible process variants, depending on the catalyst used and the remaining reaction parameters, especially the reaction temperature. However, depending on the activity of the catalyst, significantly higher space-time yields up to about 500 g $l^{-1}$ $h^{-1}$ can also be achieved.

The reaction mixture is fractionated by customary processes. These include, for example, fractional distillation, which may be performed under reduced pressure, or separation at elevated temperatures and atmospheric pressure in a falling-film evaporator. Low-boiling fractions which contain still unreacted olefins may, if desired, be.recycled to the reaction apparatus. Advantageously, in the process according to the invention, substantial conversion of the olefins present in the $C_5$ fraction to oligomers is achieved, so that the low-boilers separated off comprise a $C_5$-hydrocarbon mixture containing predominantly saturated cyclic and acyclic compounds. These may be fed to industrial use, if appropriate after further fractionation by distillation into cyclopentene and n-/isopentane mixtures. Cyclopentane is used, for example, as a substitute for the CFCs and HCFCs, which are of concern with regard to damage to the atmosphere, as blowing agent for polyurethane systems for producing hard foams. n-/isopentane mixtures serve, for example, as solvents for foaming polymers and as propellants for aerosols. The invention further relates to the cyclopentene-derived oligomer mixtures of the formula I obtained by the process according to the invention. As described above, the number and the position of the double bonds in the oligomers can be influenced by the reaction conditions, in particular the catalyst used in each case. The process according to the invention produces cyclopentene oligomers, with the iodine number being at least 250 g of $I_2$/100 g of oligomer, preferably at least 300 g of $I_2$/100 g of oligomer.

The mean molecular weight of the cyclopentene-derived oligomers is at least 274 g/mol, which corresponds to a mean reaction of three cyclopentene units per oligomer, in this case chain termination due to an acyclic pentene (and not due to a cross metathesis product) being assumed.

Particularly preferably, the oligomer mixtures of the formula I serve as intermediates for further processing by functionalization of at least some of the double bonds present therein. This can be performed in the context of a polymer-like reaction, such as by catalytic hydroformylation.

The oxo products thus obtained have a multiplicity of possible uses, eg. as additives in sealing compositions, compatibilizers, adhesives, incrustation inhibitors, polyelectrolytes, complexing agents, tanning additives, etc.

The following non-restrictive examples illustrate the invention.

EXAMPLES

Gas chromatograms were recorded using a 5890 gas chromatograph from Hewlett Packard equipped with a DB 5.30 m×0.32 mm glass capillary column and a flame ionization detector with an attached integrating unit.

Example 1

Model System

A 1:1 mixture of 17.1 mol each of cyclopentene and 1-pentene was admixed at room temperature and atmospheric pressure with an in-situ-generated catalyst mixture of 8.6 mmol of (p-cymene)$RuCl_2(PCy_3)$ and 2 ml $Me_3SiCHN_2$ in 50 ml $CH_2Cl_2$. In this case, a slight gas development was observed. After stirring for 3 hours, the solution was chromatographed on neutral $Al_2O_3$ and the colorless filtrate was freed by distillation from unreacted low-boilers. 956 g of a colorless low-viscosity liquid of the following composition (percent of GC area) remained:

26% $C_{10}H_{18}$, 22% $C_{15}H_{26}$, 17% $C_{20}H_{34}$, 13% $C_{25}H_{42}$, 10% $C_{30}H_{50}$, 7% $C_{35}H_{58}$, 5% $C_{40}H_{66}$. Iodine number: 351 g of $I_2$/100 g

Example 2

Homogeneously Catalyzed Metathesis of $C_5$ Fraction 1 l of $C_5$ fraction (cyclopentene content: 15%) was reacted at room temperature and atmospheric pressure with a solution of 0.6 mmol of $RuCl_2$(=$CHPh$)$(PCy_3)_2$ in 20 ml $CH_2Cl_2$. In this case a slight gas development was observed. After stirring for 1 h, the solution was chromatographed on $Al_2O_3$ and the colorless filtrate was freed by distillation from unreacted low-boilers. 96 g of a colorless low-viscosity liquid of the following composition (percent of GC area) were obtained: 4% $C_7H_{12}$, 11% $C_8H_{16}$, 14% $C_{10}H_{18}$, 3% $C_{12}H_{20}$, 8% $C_{13}H_{24}$, 12% $C_{15}H_{26}$, 2% $C_{17}H_{28}$, 5% $C_{18}H_{32}$, 9% $C_{20}H_{34}$, 1% $C_{22}H_{36}$, 4% $C_{23}H_{40}$, 7% $C_{25}H_{42}$, 3% $C_{28}H_{48}$, 6% $C_{30}H_{50}$, 1% $C_{33}H_{56}$, 4% $C_{35}H_{58}$, 3% $C_{40}H_{58}$, 3% $C_{40}H_{66}$, 2% $C_{40}H_{66}$, 1% $C_{40}H_{66}$. Iodine number: 329 g of $I_2$/100 g

Example 3

Model System

A 1:1 mixture of cyclopentene and 1-pentene was continuously pumped into a tubular reactor charged with $ReO_7$/$Al_2O_3$ at 60° C., 5 bar and for residence times of 1–3 h. The reaction product was then separated into a low-boiler and high-boiler fraction using a falling-film evaporator operated at 115° C. and atmospheric pressure and the low-boiler fraction was recycled to the metathesis process. The high-boiler fraction was freed under reduced pressure from residual amounts of low-boilers. At space-time yields of 50–500 g $l^{-1}$ $h^{-1}$, slightly yellowish liquids were obtained, which were then chromatographed on $Al_2O_3$. A sample taken off had the following composition (percent GC area): 3% $C_7H_{12}$, 9% $C_8H_{16}$, 16% $C_{10}H_{18}$, 2% $C_{12}H_{20}$, 8% $C_{13}H_{24}$, 13% $C_{15}H_{26}$, 2% $C_{17}H_{28}$, 6% $C_{18}H_{32}$, 11% $C_{20}H_{34}$, 1% $C_{22}H_{36}$, 4% $C_{23}H_{40}$, 9% $C_{25}H_{42}$, 2% $C_{28}H_{48}$, 6% $C_{30}H_{50}$, 3% $C_{35}H_{58}$, 2% $C_{40}H_{66}$, 1% $C_{40}H_{66}$, 1% $C_{45}H_{74}$. Iodine number:,349 g of $I_2$/100 g

Example 4

Heterogeneously Catalyzed Metathesis of $C_5$ Fraction 1 l of $C_5$ fraction was continuously pumped into a tubular reactor charged with $Re_2O_7$/$Al_2O_3$ at 60° C., 5 bar and for residence times of 1–3 h. The reaction product was separated into a low-boiler and a high-boiler fraction using a falling-film evaporator operated at 115° C. and atmospheric pressure. The high-boiler fraction was freed from residual amounts of low-boilers by distillation under reduced pressure. At space-time yields of 20–100 g $1^{-1}$ $h^{-1}$ and cyclopentene conversion rates up to 70%, slightly yellowish liquids were obtained which were then chromatographed on $Al_2O_3$. A sample taken off had the following composition (percent GC area): 4% $C_7H_{12}$, 11% $C_8H_{16}$, 14% $C_{10}H_{18}$, 3% $C_{12}H_{20}$, 8% $C_{13}H_{24}$, 12% $C_{15}H_{26}$, 2% $C_{17}H_{28}$, 5% $C_{18}H_{32}$, 9% $C_{20}H_{34}$, 1% $C_{22}H_{36}$, 4% $C_{23}H_{40}$, 7% $C_{25}H_{42}$, 3% $C_{28}H_{48}$, 6% $C_{30}H_{50}$, 1% $C_{33}H_{56}$, 4% $C_{35}H_{58}$, 3% $C_{40}H_{66}$, 2% $C_{45}H_{74}$, 1% $C_{50}H_{82}$. Iodine number: 325 g of $I_2$/100 g Example 5

1 l of $C_5$ fraction, in equimolar ratio with raffinate II, was continuously pumped into a tubular reactor charged with $Re_2O_7/Al_2O_3$ at 60° C., 11 bar and for residence times of 1–2 h. The reaction product was separated into a low-boiler and a high-boiler fraction using a falling-film evaporator operated at 100° C. and atmospheric pressure. The high-boiler fraction was freed from residual amounts of low-boilers by distillation under reduced pressure. At space-time yields of 50–200 g $1^{-1}$ $h^{-1}$ and cyclopentene conversion rates around 80%, slightly yellowish liquids were obtained which were then chromatographed on $Al_2O_3$. The samples were analyzed by GC and contained the following product families which could no longer be assigned unambiguously: $C_6H_{12}$, $C_7H_{12}$, $C_8H_{14}$, $C_9H_{16}$+individual secondary products up to $C_{49}H_{80}$. Iodine number: 35 g of $I_2$/100 g Example 6

Continuous Ethenolysis of Cyclopentene

Cyclopentene, under 30 bar of ethene, was continuously pumped into a tubular reactor charged with $Re_2O_7/Al_2O_3$ at 60° C. and for residence times of 1–2 h. The reaction product was separated into a low-boiler and a high-boiler fraction using a falling-film evaporator operated at 80° C. and atmospheric pressure. The high-boiler fraction was freed from residual amounts of low-boilers by distillation under a low vacuum. At space-time yields of 100–350 g $1^{-1}h^{-1}$ and cyclopentene conversion rates around 85%, orange-yellow liquids were obtained, which had the following composition following chromatography on $Al_2O_3$ (percent GC area): 29% $C_7H_{12}$, 4% $C_8H_{14}$, 24% $C_{12}H_2O$, 3% $C_{13}H_{22}$, 17% $C_{17}H_{28}$, 1% $C_{18}H_{30}$, 12% $C_{22}H_{36}$, 1% $C_{23}H_{38}$, 8% $C_{27}H_{44}$, 1% higher olefins. Iodine number: 384 g of $I_2$/100 g Example 7

Heterogeneously Catalyzed Batch Ethenolysis of $C_5$ Fraction 60 ml of $C_5$ fraction were treated with 30 bar ethene at room temperature in a 100 ml pressure vessel which is charged with 10 g of $Re_2O_7/Al_2O_3$. After heating to 60° C., ethene was forced in up to a total pressure of 70 bar and this pressure was kept constant in the further course of the reaction. After 2 h, the reaction mixture was cooled to room temperature and carefully depressurized. The colorless solution thus obtained had, after removal of the low-boilers by distillation, the following composition (percent GC area): 16% $C_7H_{12}$, 12% $C8H_{14}$, 6% $C_9H_{16}$, 2% $C_{10}H_{18}$, 14% $C_{12}H_{20}$, 9% $C_{13}H_{22}$, 3% $C_{14}H_{24}$, 1% $C_{15}H_{26}$, 9% $C_{17}H_{28}$, 6% $C_{18}H_{30}$, 2% $C_{19}H_{32}$, 6% $C_{22}H_{36}$, 2% $C_{23}H_{38}$, 4% $C_{27}H_{44}$, 8% higher olefines Yield: 11 g of oligomers Iodine number: 376 g of $I_2$/100 g Example 8

Homogeneously Catalyzed Batch Ethenolysis of $C_5$ Fraction

In a 100 ml pressure vessel, 60 ml $C_5$ fraction were admixed at room temperature with a solution of 84 mg (0.10 mmol) of $RuCl_2$(=CHPh)$(PCy_3)_2$ in 2 ml of $CH_2Cl_2$ and immediately pressurized to 70 bar with ethene. The pressure was kept constant during further course of the reaction by regularly forcing in ethene. After stirring for 1 h at room temperature, the reaction mixture was carefully depressurized. The colorless solution thus obtained, after separating off the low-boilers by distillation, had the following composition (per cent GC area): 13% $C_7H_{12}$, 12% $C_8H_{14}$, 6% $C_9H_{16}$, 1% $C_{10}H_{18}$, 10% $C_{12}H_{20}$, 11% $C_{13}H_{22}$, 4% $C_{14}H_{24}$, 9% $C_{17}H_{28}$, 8% $C_{18}H_{30}$, 3% $C_{19}H_{32}$, 4% $C_{23}H_{38}$, 3% $C_{27}H_{44}$, 10% higher olefins. Yield: 12 g of oligomers Iodine number 372 g of $I_2$/100 g 183/hz

We claim:

1. A process for the work-up of a $C_5$ fraction which contains cyclopentane, cyclopentene and acyclic monoolefins, comprising (1) reacting the $C_5$ fraction, in a homogeneously or heterogeneously catalyzed metathesis reaction, to produce a reaction mixture including oligomers preparing oligomer mixtures of the formula I

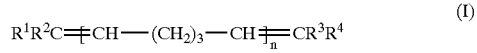

$$R^1R^2C=\!\!\!=\!\!\!\!{\underset{n}{\vphantom{|}\mathrm{CH-\!\!\!-(CH_2)_3-\!\!\!-CH}}}\!\!\!\!=\!\!\!=CR^3R^4 \qquad (I)$$

where n is an integer from 1 to 15, and $R^1, R^2, R^3, R^4$ independently of one another are hydrogen or alkyl, (2) fractionating the reaction mixture to obtain low-boiling fractions, (3) separating off a low-boiling fraction that contains cyclopentane.

2. A process as claimed in claim 1, wherein the metathesis reaction consists of a) the disproportionation of the acyclic monoolefins of the $C_5$ fraction by cross metathesis, b) the oligomerization of the cyclopentene by ring-scission metathesis, and c) chain termination by reacting the oligomers from b) with an acyclic olefin of the $C_5$ fraction or of a product from a), wherein any one or all of the steps a), b) and c) may be repeated.

3. The process as claimed in claim 1, wherein a $C_5$ fraction having a total olefin content of at least 30% by weight is used.

4. The process as claimed in claim 3, wherein a $C_5$ fraction having a cyclopentene content of at least 10% by weight is used.

5. The process as claimed in claim 3, wherein a $C_5$ fraction is used, with the acyclic monoolefins having a content of pentene isomers of at least 80% by weight.

6. The process as claimed in claim 1, wherein a petroleum fraction containing acyclic $C_4$ olefins (raffinate 2) is added to the $C_5$ fraction prior to step (1).

7. The process as claimed in 1, claim wherein ethene is added to the $C_5$ fraction prior to step (1).

8. A process as claimed in claim 7, wherein the reaction is carried out at a pressure of from 1 to 200 bar.

9. A process as claimed in claim 7, wherein the reaction is carried out at a pressure of from 20 to 150 bar.

10. A process as claimed in claim 7, wherein the reaction is carried out at a pressure of from 40 to 100 bar.

11. A process as claimed in claim 1, wherein a catalyst is used which comprises at least one transition metal of subgroups 6, 7 or 8.

12. A process as claimed in claim 11, wherein a catalyst is used which comprises
   a) at least one transition metal-alkylidene complex (transition metal-carbon complex) or
   b) a combination, suitable for forming a complex a), of a transition metal compound and at least one further agent, preferably an alkylating agent, or
   c) a transition metal compound suitable for forming a complex a) with the olefins present in the hydrocarbon mixture.

13. The process as claimed in claim 11, wherein a homogeneous catalyst is used which is selected from the group consisting of (a) ruthenium-alkylidene complexes of the formula $$RuCl_2(=CHC_6H_5)(P(C_6H_{11})_3)_2,$$

(b) molybdenum-alkylidene complexes, (c) $CH_3ReC_3/C_2H_5AlCl_2$, (d) $WOCl_2(O\text{-}(2,6\text{-}Br_2\text{-}C_6H_3))/Sn(CH_3)_4$, (e) $WCl_6/C_2H_5AlCl_2(Sn(CH_3)_4)/EtOH$, and (f) $WOCl_4/Sn(CH_3)_4$.

14. A process as claimed in claim 11, wherein a heterogeneous catalyst is used which is selected from the group consisting of $Re_2O_7$ and $CH_3ReO_3$ on an inorganic support.

15. The process of claim 1 further comprising
   4) separating off a low-boiling fraction containing unreacted olefins, and
   5) recycling said fraction into step 1).

* * * * *